(12) United States Patent
Zhang et al.

(10) Patent No.: US 7,752,002 B2
(45) Date of Patent: Jul. 6, 2010

(54) METHODS AND APPARATUS FOR NON-INVASIVE IMPLANTABLE PRESSURE SENSOR CALIBRATION

(75) Inventors: Yang Zhang, Huntington Beach, CA (US); Yongning Zou, Valencia, CA (US); Dan E. Gutfinger, Agoura Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 116 days.

(21) Appl. No.: 12/130,789

(22) Filed: May 30, 2008

(65) Prior Publication Data

US 2009/0299672 A1 Dec. 3, 2009

(51) Int. Cl.
*G01L 27/00* (2006.01)
*A61B 5/08* (2006.01)
(52) U.S. Cl. ........................................ 702/98; 600/532
(58) Field of Classification Search ................... 702/85, 702/98; 600/485, 486; 607/23, 44; 604/9
See application file for complete search history.

(56) References Cited

U.S. PATENT DOCUMENTS

| 4,076,021 | A  | * | 2/1978  | Thompson .............. 128/205.18 |
| 5,361,771 | A  | * | 11/1994 | Craine et al. ................. 600/532 |
| 2004/0204655 | A1 | * | 10/2004 | Stock et al. .................. 600/532 |
| 2008/0262361 | A1 | * | 10/2008 | Gutfinger et al. ............ 600/486 |

* cited by examiner

*Primary Examiner*—Bryan Bui (57) ABSTRACT

An economical, repeatable, and non-invasive method and apparatus for the calibration of implantable pressure sensors that can minimize patient discomfort and risk of infection. In one embodiment, a calibration system for calibrating a first pressure sensor coupled to a management device and implanted into a human patient is provided. The calibration system includes a mouthpiece, a pump, a second pressure sensor, and a computer. The pump provides a positive pressure into an airway of the human patient via the mouthpiece. The second pressure sensor measures the airway pressure of the human patient, and the computer is coupled to the pump and monitors pressures measured by the first and second pressure sensors. Here, the computer also calculates one or more calibration constants based on the pressures measured by the first and second pressure sensors and provides the calibration constants to the management device to calibrate the first pressure sensor.

15 Claims, 9 Drawing Sheets

METHODS AND APPARATUS FOR NON-INVASIVE IMPLANTABLE PRESSURE SENSOR CALIBRATION

TECHNICAL FIELD

This invention relates to calibration of implantable pressure sensors.

BACKGROUND

Measurements of heart chamber pressure, e.g., left atrial pressure (LAP), are useful for monitoring heart failure. If the LAP is abnormally high, a human patient will experience fatigue, shortness of breath, fluid build up in multiple areas of the body, and weight gain. Implantable pressure sensors (e.g., piezoelectric crystals and optical, capacitance, inductance, electrolytic, and/or resistive strain gauge manometers) are available to measure LAP so necessary medications can be taken to thus form a closed loop treatment system for managing heart failure. Due to tissue growth around the implanted sensor, electrical and mechanical shock, changes of ambient pressure, material creep, and aging of components, an implanted pressure sensor may drift and have an offset that may skew the pressure data measured by the implanted pressure sensor.

If the pressure reading is skewed, the patient may not get the proper treatment. As such, there is a need to ensure the pressure measured by the implanted sensor is the actual pressure within the heart. Thus, the implantable cardiac pressure sensor needs to be calibrated periodically after the implantation.

In one calibration method and apparatus, it is required that an implanted pressure sensor be exposed to atmospheric pressure in order to calibrate the sensor, thus requiring an invasive and/or uncomfortable procedure to access the sensor. As such, there is a need for a calibration method and apparatus of an implantable pressure sensor that minimizes patient discomfort, is not invasive, and/or does not require a percutaneous access to the sensor in order to calibrate it.

In one non-invasive calibration method and apparatus, a human patient is required to perform multiple Valsalva maneuvers for 8-10 seconds to complete the calibration of an implanted pressure sensor. However, in this method and apparatus, it is difficult (or impossible) for the patient with heart failure having an episode of congestive heart failure exacerbation with pulmonary edema to perform multiple Valsalva maneuvers due to symptoms of the disease. In addition, the patient may be subject to the risk of cross infection from the tubes and/or chambers utilized by the calibration apparatus if the apparatus is shared. On the other hand, if the patient applies too much pressure while doing the Valsalva maneuvers, the patient may feel dizzy or faint, get a hernia, damage alveolar sacs within the lungs, and/or get a punctured lung.

Accordingly, there is a need for an economical, repeatable, and non-invasive method and apparatus for the calibration of implanted pressure sensors that can minimize patient discomfort and the risk of infection.

SUMMARY

A summary of selected aspects and/or embodiments of an apparatus constructed or a method practiced according to the invention follows. For convenience, an embodiment of an apparatus constructed or a method practiced according to the invention may be referred to herein simply as an "embodiment."

The invention relates in one aspect to an economical, repeatable, and non-invasive method and apparatus for the calibration of implanted pressure sensors that can minimize patient discomfort and the risk of infection.

In one embodiment, a calibration system for calibrating a first pressure sensor (e.g., a left atrial pressure sensor) coupled to a management device and implanted into a human patient is provided. The calibration system includes a mouthpiece, a pump, a second pressure sensor, and a computer. The mouthpiece is adapted to provide a positive pressure into an airway of the human patient. The pump is adapted to provide the pressure to the mouthpiece. The second pressure sensor is adapted to measure the airway pressure of the human patient, and the computer is coupled to the pump and adapted to monitor pressures measured by the first pressure sensor and the second pressure sensor. Here, the computer is also adapted to calculate at least one calibration constant based on the pressures measured by the first pressure sensor and the second pressure sensor and to provide at least one calibration constant to the management device coupled to the first pressure sensor to calibrate the first pressure sensor.

In another embodiment, a method of calibrating a first pressure sensor coupled to a management device and implanted into a human patient is provided. The method includes: placing a mouthpiece on the human patient; pumping air into the lung of the human patient through the mouthpiece; measuring at least one first pressure using the first pressure sensor implanted in the human patient; measuring at least one second pressure using a second pressure sensor external to the human patient; calculating at least one calibration constant based on the first pressure and the second pressure; and providing at least one calibration constant to the management device coupled to the first pressure sensor to calibrate the first pressure sensor.

BRIEF DESCRIPTION OF THE DRAWINGS

These and other features, aspects and advantages of the invention will be more fully understood when considered with respect to the following detailed description, appended claims and accompanying drawings, wherein:

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

Aspects of the invention are described below, with reference to detailed illustrative embodiments. It will be apparent that the invention may be embodied in a wide variety of forms, some of which may be quite different from those of the disclosed embodiments. Consequently, the specific structural and/or functional details disclosed herein are merely representative and do not limit the scope of the invention.

For example, based on the teachings herein one skilled in the art should appreciate that the various structural and/or functional details disclosed herein may be incorporated in an embodiment independently of any other structural and/or functional details. Thus, an apparatus may be implemented and/or a method practiced using any number of the structural and/or functional details set forth in any disclosed embodiment(s). Also, an apparatus may be implemented and/or a method practiced using other structural and/or functional details in addition to or other than the structural and/or functional details set forth in any disclosed embodiment(s). Accordingly, references to "an" or "one" embodiment in this discussion are not necessarily to the same embodiment, and such references mean at least one embodiment.

An implantable pressure sensor may be implanted to determine pressure at a location anywhere within a thoracic cavity of a human patient. Pressure sensors suitable for such use include, but are not limited to piezoelectric crystals; optical, capacitance, inductance, electrolytic, and/or resistive strain gauge manometers; and microelectromechanical systems (MEMS).

In one embodiment, such pressure sensors are made from a variety of materials suitable for converting a mechanical strain into an electrical signal. One example of such sensor is a silicon resistor. The sensor size is appropriate to generate a detectable signal with adequate resolution.

In one embodiment, the pressure sensor has a hermetically sealed housing. The sensor housing may have a titanium cylinder hermetically closed at both ends and filled with a gas. The cylinder may have a diameter from about 1 to about 4 mm and a length of about 3 to about 15 mm.

One end of the cylinder may be sealed by a diaphragm that is mechanically coupled to one or more strain gauges inside the housing. The diaphragm may be a titanium foil with a thickness of about 1 to 3 mils. The strain gauges may be adhered to the inside surface of the diaphragm. The strain gauges may be resistive strain gauges.

In one embodiment, two or four resistive strain gauges are attached to the diaphragm and electrically connected to form a half or full Wheatstone bridge, respectively. The voltage across the bridge is proportional to the imbalance of strain-induced resistance between the sides of the bridge, and thereby indicates the pressure-induced strain in the diaphragm. In one embodiment, electronic circuitry is disposed within the housing that operates to measure the voltage across the bridge and to convert this voltage to a signal indicative of the pressure on the outside of the diaphragm.

The other end of the housing may be sealed by a feedthrough insulator with one or more electrical conductors. The hermetically sealed feedthrough insulator may be a ceramic material with two electrical conductors. Alternatively, the hermetically sealed feedthrough insulator may have one electrical conductor.

Figure 1:
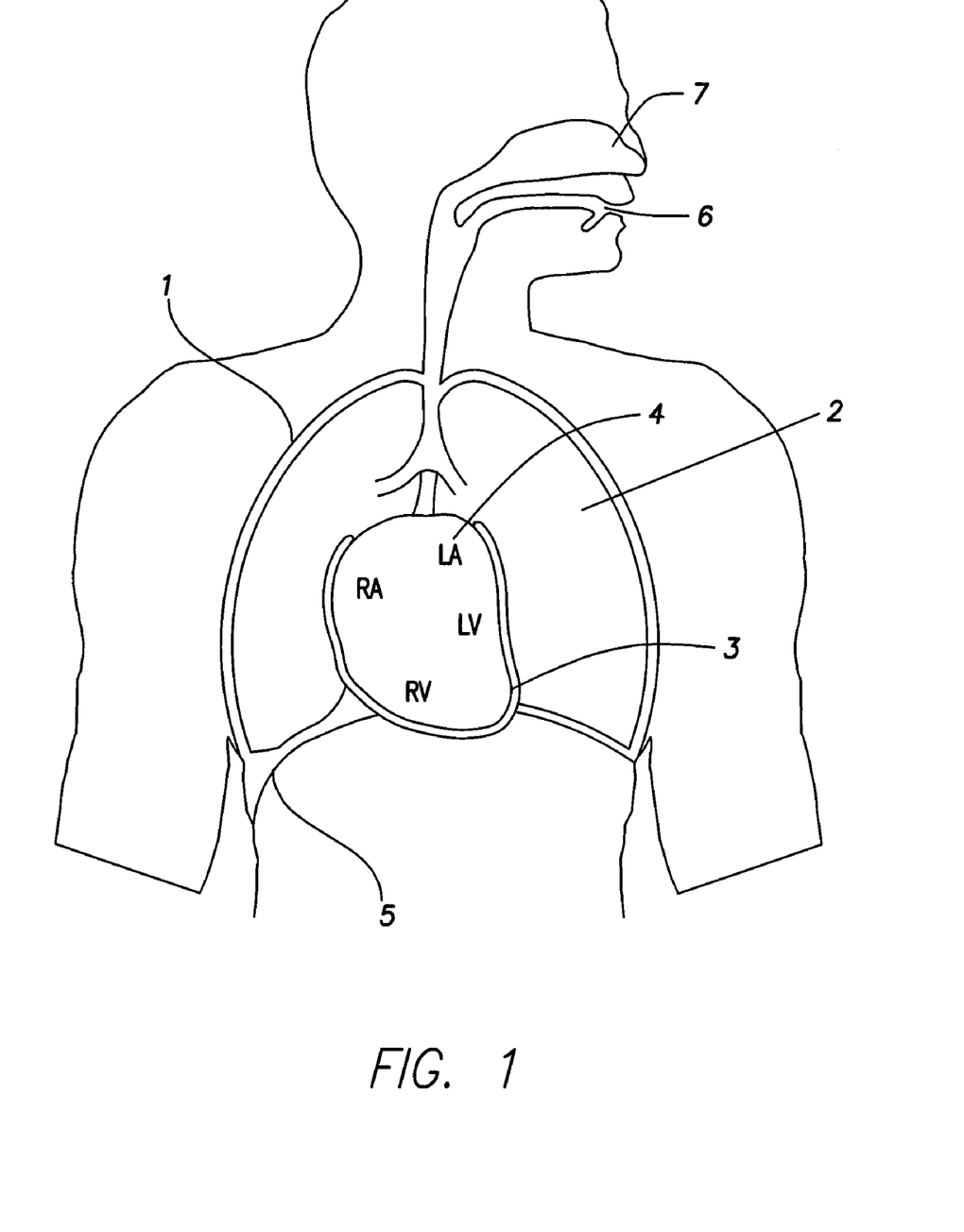
FIG. 1 is a simplified diagram of the thoracic cavity with heart and lungs of a human patient.

Referring to FIG. 1, in one embodiment, at least one sensor as described above is implanted inside of a human patient to determine the pressure at any suitable location within the thoracic cavity of the patient. Such intra-thoracic locations include, but are not limited to, the pleural space 1, the lungs 2, the pericardial space 3 and the heart 4 including its four chambers, i.e., right atrium (RA), right ventricle (RV), left atrium (LA), and left ventricle (LV). In some embodiments, pressure sensors can be placed in any location, including but not limited to, the blood and lymphatic vessels, the mediastinum, and the esophagus. In other embodiments, pressure sensors can be placed in a structure of the heart, or a cavity of the heart, including the left or right atrium, and the left or right ventricle. In another embodiment, pressure sensors are placed in the pulmonary vein or artery, the coronary sinus, the superior vena cava, the thoracic portion of a subclavian vein, the jugular vein, the intrathoracic portion of the inferior vena cava, or the intrathoracic portion of any vein. In other embodiments, pressure sensors are placed in the aorta, the intrathoracic portion of any artery, the intrathoracic portion of any blood vessel, the pleural space, the pericardial space, the esophagus, the pulmonary parenchyma, the pulmonary airspaces, the upper airway of the nasopharynx, the intrathoracic portion of a lymphatic duct, the intrathoracic portion of any body structure, or the intrathoracic portion of any device placed within the body.

Intrathoracic and nasopharangeal sites, under certain conditions, such as a Valsalva maneuver, reflect intrathoracic pressure. For the purposes of illustrative example, one or more sensors are implanted by an invasive or surgical procedure for the clinical purpose of measuring pressure at first locations known to be indicative of filling of the heart with blood and that aid in diagnosing and treating illnesses such as congestive heart failure. These locations can include the left ventricle, the left atrium, the pulmonary veins, the pulmonary capillaries, the pulmonary arteries, the right ventricle, and the right atrium.

With the exclusion of certain well-known medical conditions, a key parameter for determining the state of the heart is the left atrial pressure (LAP). LAP is closely predicted by or is clinically equal with the pulmonary venous pressure (PVP). These pressures are complex periodic time varying signals composed of the superposition of cardiac and respiratory component waves. During normal and certain pathologic conditions such as congestive heart failure, these pressures typically vary from 0 to 40 mm Hg gauge pressure referenced to atmospheric pressure. With few exceptions, during a normal breathing, these pressures transiently decrease during inspiration and increase with exhalation coincident with changes in intrathoracic pressure caused by respiratory muscle contraction including diaphragm 5 (FIG. 1) and chest wall and lung elastic recoil. These pressures have exaggerated increases in response to sudden perturbations in intrathoracic pressure that can result from exaggerated breathing, coughing, sneezing or straining, etc.

In one embodiment, a method to induce a Valsalva maneuver is provided, such that the maneuver causes a first pressure to have a calculable relationship with a second pressure. The Valsalva maneuver (or Valsalva) can be used to transiently perturb cardiovascular and other physiology for diagnostic clinical purposes. The Valsalva maneuver includes a forced expiratory effort against a closed glottis to create the transient perturbation. Typically, a person performing the Valsalva maneuver can maintain upper airway pressure of at least 40 mm of Hg for up to 30 seconds. The Valsalva maneuver increases pressure within the thoracic cavity and thereby impedes venous return of blood to the heart. It has complex physiologic effects on heart rate, arterial blood pressure, and filling of the heart's chambers.

In one embodiment, multiple Valsalva maneuvers (or different Valsalva maneuvers) are induced to produce a plurality of distinct values of airway pressure, e.g., performing phase I of a Valsalva maneuver, which generates the initial rise in intrathoracic pressure, and performing phase II of a Valsalva maneuver, also referred to as the plateau phase, which sustains the elevation in intrathoracic pressure.

In one embodiment, an artificially induced Valsalva maneuver by applying positive pressure ventilation and maintaining the pressure ventilation for a period of time is provided. In one embodiment, this artificially induced Valsalva maneuver (hereafter also referred to as just Valsalva maneuver or Valsalva) is enhanced by using, substantially simultaneously, externally or internally applied abdomen pressure to further raise intrathoracic pressure. The pressure rise can be serially stepped to different levels, such as, for example, but not limited to, 40, 50, and 60 mm Hg. When the maneuver is completed (usually after about 10 to about 20 seconds) the patient resumes normal unassisted or assisted breathing, as prior to the maneuver.

In one embodiment, a second, less-invasively located, calibrated pressure sensor measuring airway pressure or some other pressure, which under certain conditions is indicative of thoracic pressure, is used to determine the calibration of a first pressure sensor implanted within the thoracic cavity. In one embodiment, a dual sensor system is provided to calibrate a pressure sensor located inside of a human patient.

More specifically, in one embodiment of the present invention, rather than relying on a human patient to perform a Valsalva maneuver on his or her own, a computer controlled pump is used to create a precise Valsalva maneuver. As such, this embodiment provides a non-invasive method and apparatus for calibrating an implanted pressure sensor, such as a cardiac pressure sensor, a left atrial pressure (LAP) sensor, etc.

In one embodiment, a calibration system of the present invention includes a facemask or breathing tube, a plurality of valves and tubes to prevent cross infection, a ventilator or pump with an integrated external reference pressure sensor, and a computer that can control the ventilator or pump. Also, the calibration system has a telemetry mechanism that can communicate directly or indirectly with the implanted pressure sensor to obtain pressure readings, and a software module that is implemented in the computer to compute the calibration constants for the implanted pressure sensor. Additionally, an abdomen strap with an optional pump may also be included to keep the patient's diaphragm from expanding. As such, this calibration system is a closed-loop system that minimizes patient's effort in performing the Valsalva maneuver while stabilizing the pressure applied to the patient's lungs to allow accurate calibration of the implanted pressure sensor.

In operation, the patient would connect his airway to the calibration system via the face mask or breathing tube. The ventilator or pump would inflate the patient's lungs to programmed pressure levels. The calibration constants are found when the pressure in the airway equalizes with the PVP, which closely predicts or is clinically equal to the LAP.

Figure 2:
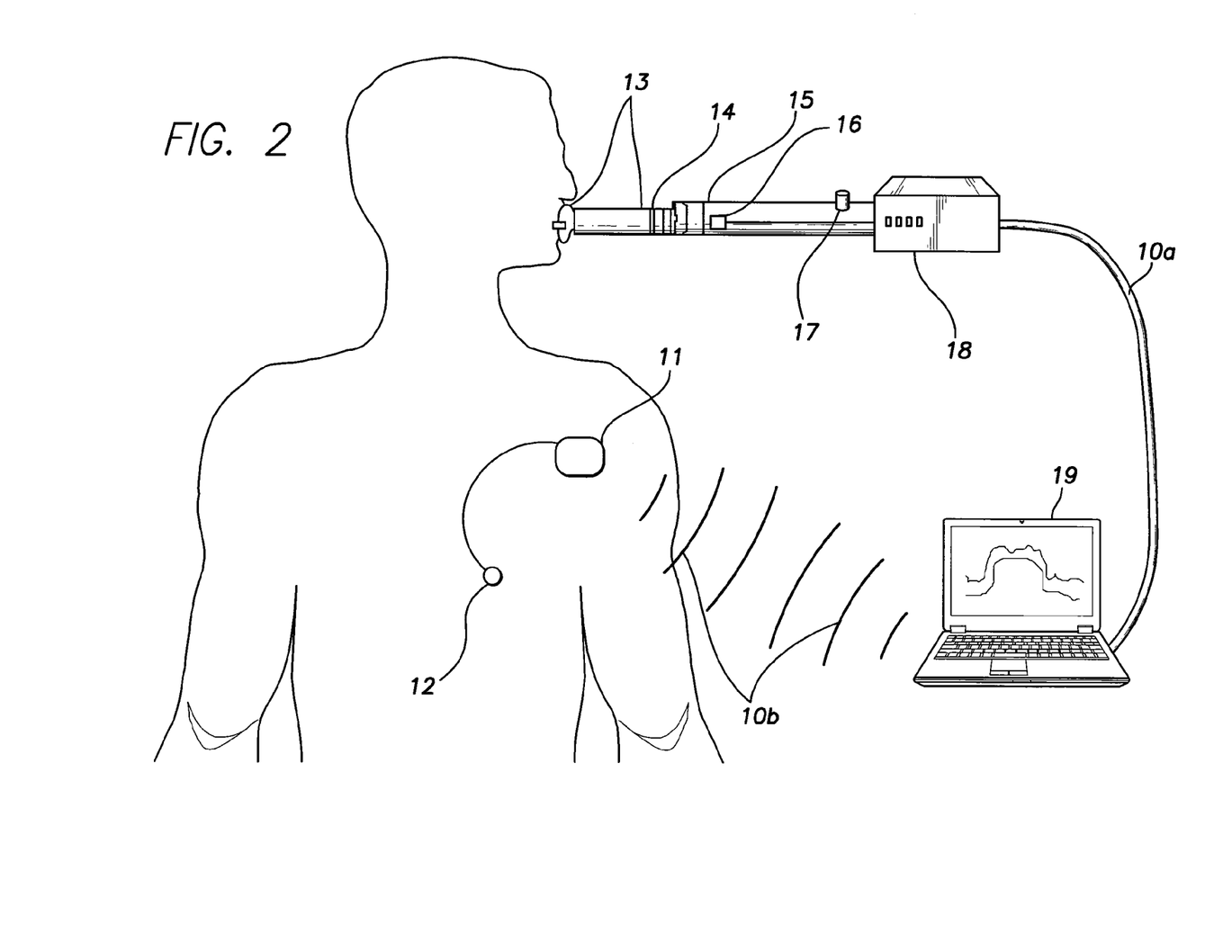
FIG. 2 is a simplified diagram of one embodiment of an implantable sensor calibration system (e.g., a left atrial pressure sensor calibration system)

In more detail, FIG. 2 shows a human patient with a management device (e.g., a cardiac rhythm management (CRM) device) 11 coupled to a first pressure sensor (e.g., an implanted left atrial pressure sensor) 12 implanted within the heart of the patient. The management device 11 is adapted to manage the first pressure sensor 12 (e.g., read, use, and/or calibrate the first pressure sensor 12). In FIG. 2, a calibration system in accordance with one embodiment of the present invention is shown to include a mouthpiece (e.g., a rubber mouthpiece or a disposable mouthpiece or a mask) 13 connected with a pump (e.g., a ventilator or an air pump) 18 through a bacterial air filter 14 and an optional one-way valve 15. A second pressure sensor (e.g., an external reference pressure sensor) 16 is connected to the ventilator or pump 18 to measure the airway pressure of the patient which will stabilize to be equal to the LAP. A pressure release valve 17 may also be placed in the system (e.g., in an air tube) to prevent over-pressure. A computer (e.g., a personal computer or a laptop computer) 19 then calculates the calibration constants and transmits the data to the CRM device 11 via a wireless communication link 10$b$ to calibrate the first or implanted pressure sensor 12.

Figure 3:
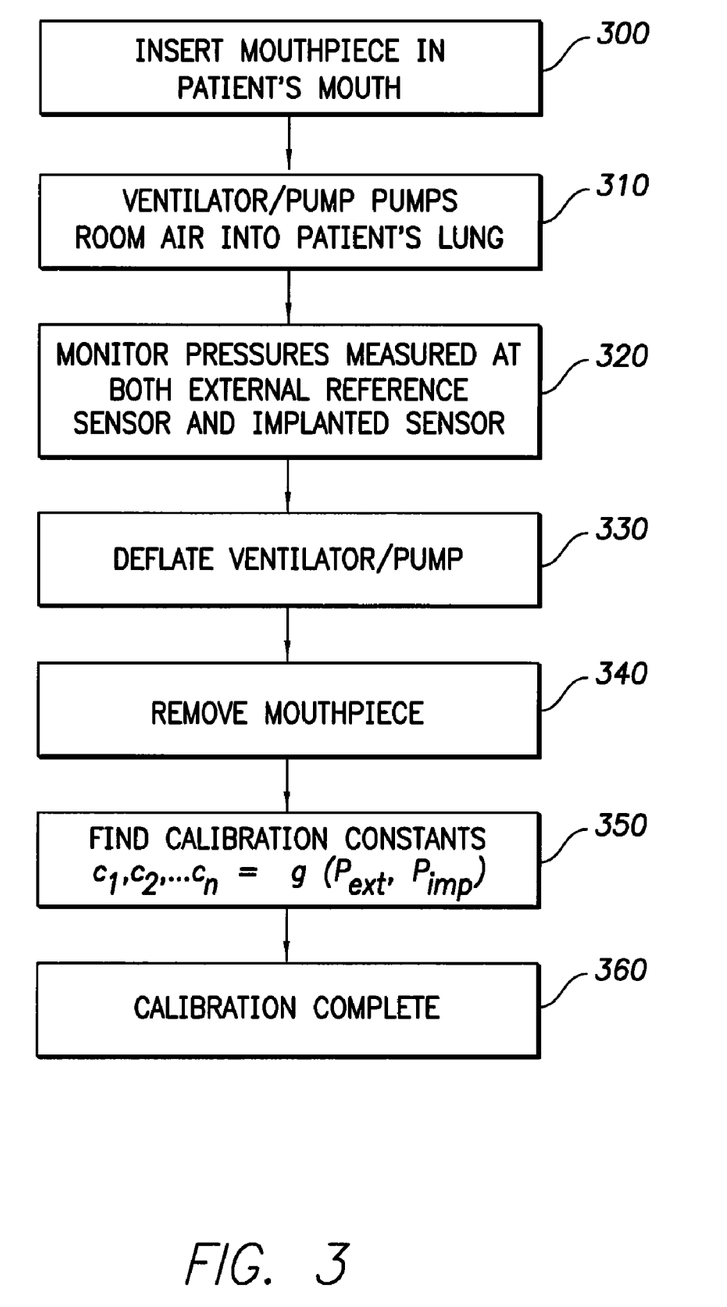
FIG. 3 is a simplified flow diagram of one embodiment of a method of calibrating an implantable sensor.

In operation and referring also to the flow diagram of FIG. 3, the patient would be instructed to relax and the disposable mouthpiece 13 would be inserted into patient's mouth 6 (FIG. 1) such that no air can escape through the patient's mouth 6 at functional block 300. Also, to prevent air escaping from the patient's nasal passage 7 (FIG. 1), a nose clip (not shown) may be provided or the patient may be instructed to pinch his nasal passage 7 with his fingers. The ventilator or pump 18 then applies pressure and pumps room air through an air tube to the patient at functional block 310. The tube contains the bacterial air filter 14 to reduce or prevent any bacteria or particles from entering the patient. The tube may also contain the one-way valve 15 so air flows into but not out of the patient to minimize cross infection. The pressure release valve 17 is also present to prevent over-pressure. The second or external reference pressure sensor 16 within the air tube then measures the pressure in the air tube which is equivalent to the airway pressure of the patient. The computer 19 monitors the airway pressure through a communication link (e.g., a wired communication link) 10$a$ connected to the ventilator or pump 18, and the computer 19 monitors the implanted sensor pressure through the wireless link 10$b$ to the CRM device 11 at functional block 320. The computer 19 then increases the ventilator or pump pressure periodically while the data from both sensors 12 and 16 are recorded. The ventilator or pump 18 is then deflated to bring down the pressure of the patient's lung at functional block 330. The patient then takes off the mouthpiece 13 at functional block 340. The computer 19 calculates the calibration constants, gain ($\alpha$) and offset ($\beta$) based on $P_{imp}=\alpha P_{ext}+\beta$ through regression analysis or some other suitable method at functional block 350. To complete the calibration, the calibration constants are then sent across the wireless link 10$b$ to the CRM device 11 to calibrate the sensor 12 at functional block 360.

Figure 4:
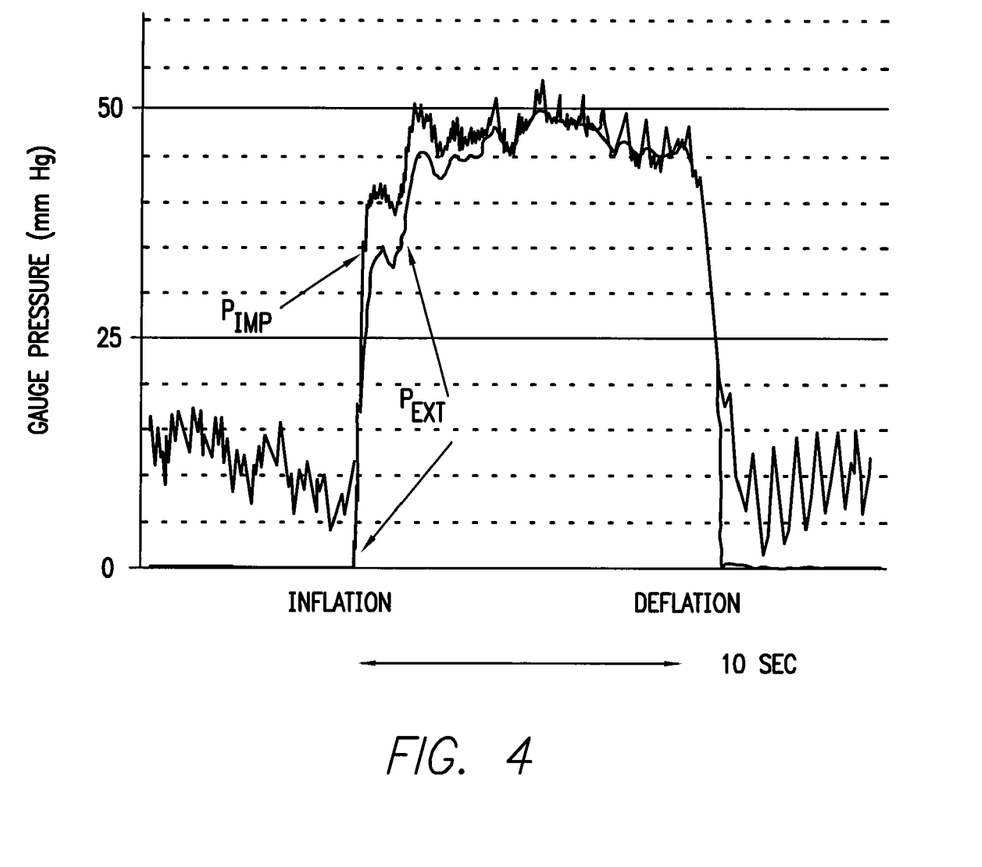
FIG. 4 is a graph of one embodiment of the difference or similarity between implanted sensor pressure ($P_{imp}$) and external sensor pressure ($P_{ext}$) versus time after initiation of a Valsalva maneuver.

More specifically, the second pressure sensor 16 is electronically connected to the computer 19 (e.g., a physiologic recorder) with a real-time video monitor displaying the measured pressures as shown in FIG. 4. Thus, the patient can have a visual feedback of the effectiveness of the ventilator or pump 18 to create the precise Valsalva maneuver on airway pressure.

In one embodiment, the ventilator or pump 18 would inflate the patient's lungs to programmed pressure levels for approximately 10 seconds. The ventilator or pump 18 would maintain the airway pressure at above about 40 mm Hg during this period. Simultaneous tracings of first and second sensor pressures and the electrocardiogram are recorded and analyzed. In one embodiment, the pressure differential between the first and second sensors is analyzed during the equilibrium Phase II of the Valsalva. In another embodiment, the pressure differential during the dynamic change in pressure introduced during the initial transient Phase I of the Valsalva is analyzed.

In more detail, during a calibration process in accordance with one embodiment of the present invention, two sets of data are collected. That is, when the pressure in the airway stabilizes during the calibration, the second, or external reference sensor pressure $P_{ext}$ and the first or implanted pressure sensor pressure $P_{imp}$ are collected (or measured) while the ventilator or pump 18 increases pressure periodically. The following regression analysis, as an example, is then performed to calculate sensor gain $\alpha$ and offset $\beta$ based on $P_{imp} = \alpha P_{ext} + \beta$. That is, a least square error is first derived and minimized as follows:

$$E = \sum_{i=1}^{n} [P_{imp_i} - (\alpha(P_{ext_i}) + \beta)]^2 = \min$$

$$\frac{dE}{d\alpha} = -2\sum_{i=1}^{n} P_{ext_i} [P_{imp_i} - (\alpha(P_{ext_i}) + \beta)] = 0$$

$$\frac{dE}{d\beta} = -2\sum_{i=1}^{n} [P_{imp_i} - (\alpha(P_{ext_i}) + \beta)] = 0$$

As such, the coefficients $\alpha$ and $\beta$ can then be found by solving a set of linear equations as follows:

$$\sum_{i=1}^{n} P_{imp_i} = \alpha \sum_{i=1}^{n} P_{ext_i} + n\beta$$

$$\sum_{i=1}^{n} P_{ext_i} P_{imp_i} = \alpha \sum_{i=1}^{n} P_{ext_i}^2 + \sum_{i=1}^{n} P_{ext_i} \beta$$

FIG. 4 shows an example of simultaneous recordings of the external reference sensor pressure $P_{ext}$ and the implanted pressure sensor pressure $P_{imp}$ as a function of time before, during and after the phases of the Valsalva maneuver. Here, at the inflation of the Valsalva maneuver (Phase I), upper airway pressure abruptly rises, and is maintained at greater than about 40 mm Hg for more than about 10 seconds (plateau or Phase II), and then upon deflation, airway pressure falls abruptly to its baseline of zero gauge pressure (atmospheric pressure).

Here, prior to the Valsalva maneuver, the implanted pressure sensor pressure $P_{imp}$ averages less than about 20 mm Hg. At the initiation of the Valsalva maneuver, the implanted pressure sensor pressure $P_{imp}$ increases coincidentally with rising of the external reference sensor pressure $P_{ext}$, maintaining a nearly constant differential with the external reference sensor pressure $P_{ext}$ during its initial rapid rise. Over the next three to four seconds the implanted pressure sensor pressure $P_{imp}$ then declines relative to the external reference sensor pressure $P_{ext}$ remaining nearly equal to the external reference sensor pressure $P_{ext}$ during the remainder of the plateau phase. Upon the deflation, the external reference sensor pressure $P_{ext}$ and the implanted pressure sensor pressure $P_{imp}$ return to baseline values.

As shown in FIG. 4, there is a time-dependent relationship between first and second sensor pressures, with the two pressures approaching equivalency about four seconds into the plateau phase of the Valsalva maneuver for the patients with pre-Valsalva first pressure below 20 mm Hg. In one embodiment, a first pressure sensor implanted to measure pressure in a first location within a human patient is calibrated by measuring a second or external reference sensor pressure at a second location during one or more Valsalva maneuvers and making use of known relationship(s) between the pressures at these first and second locations after they have equilibrated during the plateau phase of the Valsalva.

One skilled in the art will understand that other methods of analysis can also be used in accordance with various embodiments of the current invention. Multiple algorithms can be developed that use upper airway pressure to predict other cardiac pressures, such as left ventricular pressure, right atrial pressure, and right ventricular pressure or other pressures at other first locations within the thoracic cavity.

As also described above, data from multiple Valsalva maneuvers performed at different levels of pressures can be used to obtain data sufficient to solve a system of equations for the unknown calibration parameters. Examples were given in which the sensor output was a linear function with two calibration parameters. In such a linear function case, the data from the equilibrium phase of two Valsalva maneuvers is sufficient to determine the two calibration parameters. It should be apparent to one skilled in the art that additional Valsalva maneuvers could be performed to determine the additional calibration parameters of more complex sensor output functions, such as higher order polynomial functions.

It will be apparent to one skilled in the art that other maneuvers can be used to manipulate intracardiac and intrathoracic pressures in a predictable way to allow for non-invasive in vivo calibration of implanted pressure sensors as long as the intrathoracic pressure is reduced and/or increased in known relation to the external reference sensor pressure during inspiration and/or expiration.

In one embodiment, it should be apparent to one skilled in the art from the above discussion that controlled stepping of the airway pressure (e.g., 40, 50, 60 mm Hg . . . etc.) can be used to obtain and verify calibration over a broad range of pressures.

Figure 5:
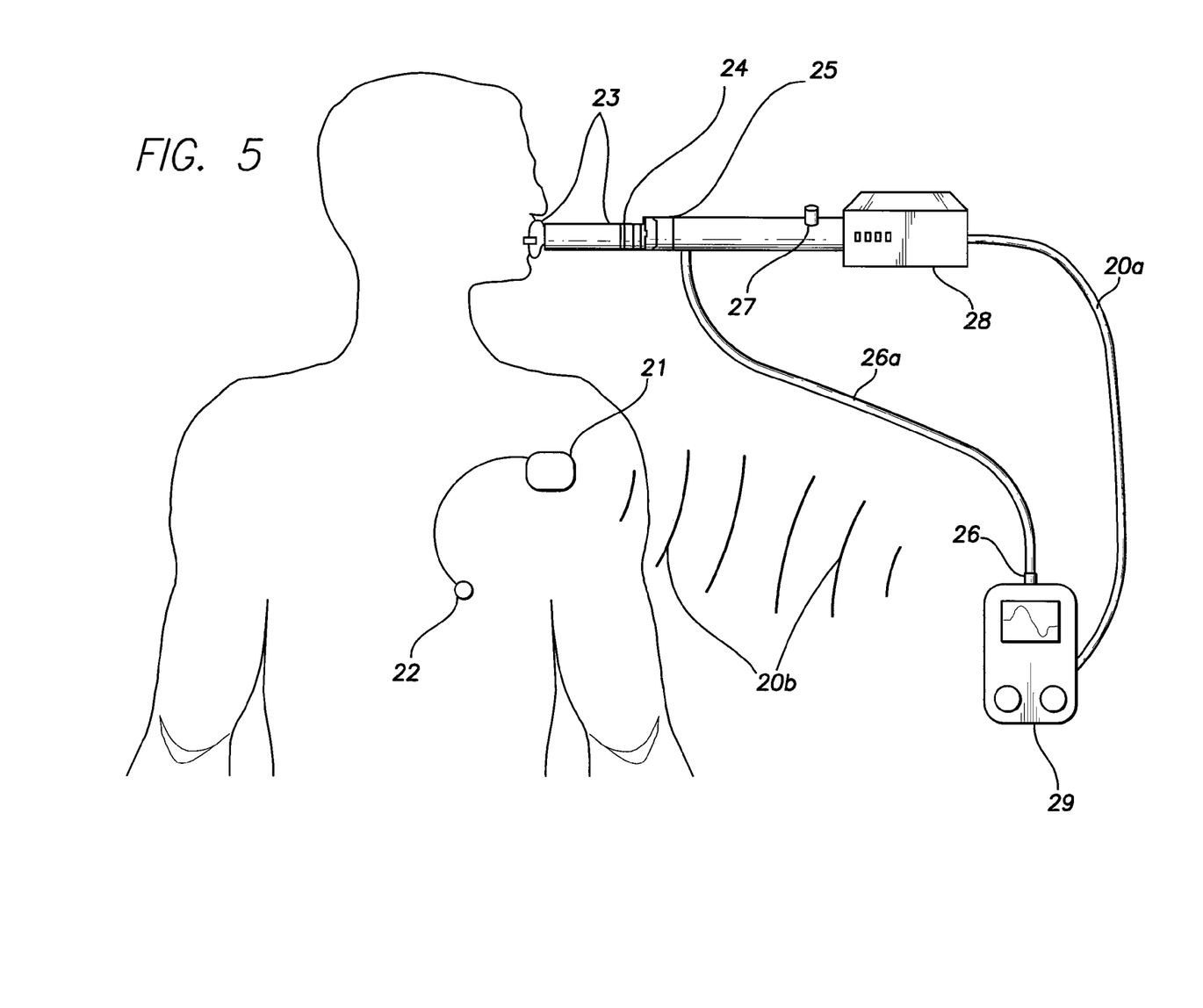
FIG. 5 is a simplified diagram of one embodiment of an implantable sensor calibration system having an external reference sensor integrated within a personal digital assistant (PDA)

Referring to FIG. 5, a calibration system in accordance with another embodiment of the present invention is provided. Here, the calibration system includes a disposable mouthpiece (e.g., a rubber mouthpiece) 23 connected with a ventilator or pump 28 through a bacterial air filter 24 and an optional one-way valve 25. A pressure release valve 27 may also be placed in the system to prevent over-pressure. A second pressure sensor (e.g., an external reference pressure sensor) 26 is connected to a computer (e.g., a personal digital assistant (PDA)) 29 to measure the airway pressure of the patient which will stabilize to be equal to the LAP. Here, the second pressure sensor 26 of the computer or PDA 29 is connected with the ventilator or pump via a link (e.g., an air tube line) 26a. The PDA 29 then calculates the calibration constants and transmits the data to a CRM device 21 for controlling or managing a first or implanted pressure sensor 22 via a wireless communication link 20b to calibrate the first or implanted pressure sensor 22.

In operation, the patient would be instructed to relax and the disposable mouthpiece 23 would be inserted into patient's mouth such that no air can escape through the patient's mouth. The ventilator or pump 28 then applies pressure and pumps room air through an air tube to the patient. The tube contains the bacterial air filter 24 to reduce or prevent any bacteria or particles from entering the patient. The tube also contains the one-way valve 25 so air flows only into but not out of the patient to minimize cross infection. The pressure release valve 27 is also present to prevent over-pressure. Here, the second or external reference pressure sensor 26 integrated within the PDA 29 then measures the pressure in the air tube via the air line 26 connected to the air tube. The measured pressure is equivalent to the airway pressure of the patient. The PDA 29 monitors the airway pressure to control the ventilator or pump 28 through a communication link (e.g., a wired communication link) 20*a*, and the PDA 29 monitors the implanted sensor pressure through the wireless link 20*b* to the CRM device 21. The PDA 29 then increases the ventilator or pump pressure periodically while the data from both sensors 22 and 26 are recorded. The patient then takes off the mask 23. The PDA 29 calculates the calibration constants, gain ($\alpha$) and offset ($\beta$) based on $P_{imp}=\alpha P_{ext}+\beta$ through regression analysis or some other suitable method. The calibration constants are then sent across the wireless link 20*b* to the CRM device 21 to calibrate the sensor 22.

Figure 6:
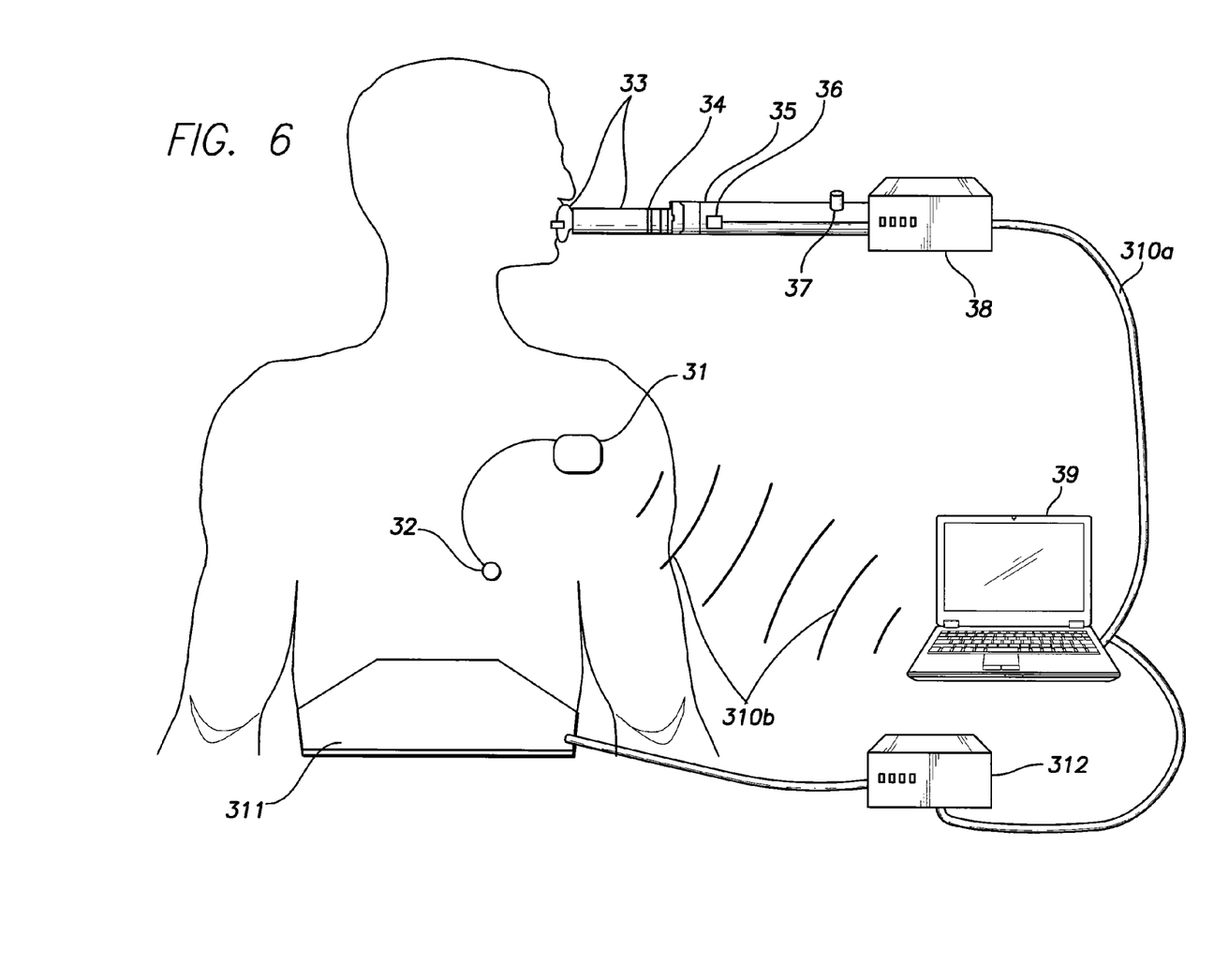
FIG. 6 is a simplified diagram of one embodiment of an implantable sensor calibration system having a pneumatic abdomen strap.

Referring to FIG. 6, a calibration system in accordance with another embodiment of the present invention includes a disposable mouthpiece (e.g., a rubber mouthpiece) 33 connected with a ventilator or pump 38 through a bacterial air filter 34 and an optional one-way valve 35. A second pressure sensor (e.g., an external reference pressure sensor) 36 is connected to the ventilator or pump 38 to measure the airway pressure of the patient which will stabilize to be equal to the LAP. A pressure release valve 37 may also be placed in the system to prevent over-pressure. A second pump 312 controlled by a computer 39 inflates a pneumatic abdomen strap (e.g., a pneumatic Velcro abdomen strap) 311. The computer 39 then calculates the calibration constants and transmits the data to a CRM device 31 for controlling or managing a first or implanted pressure sensor 32 via a wireless communication link 310*b* to calibrate the first or implanted pressure sensor 32.

Figure 7:
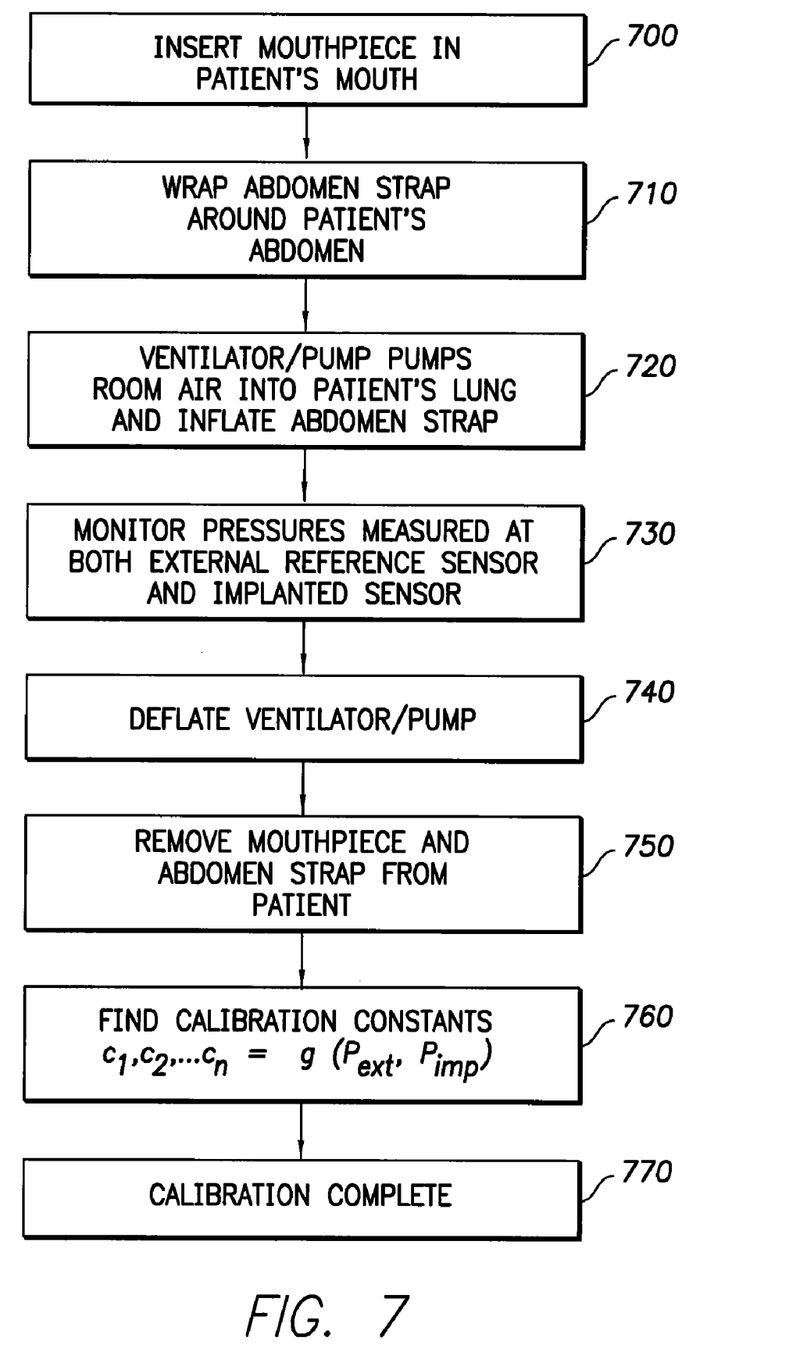
FIG. 7 is a simplified flow diagram of one embodiment of a method of calibrating an implantable sensor using an abdomen strap.

In operation and referring also to the flow diagram of FIG. 7, the patient would be instructed to relax and the disposable mouthpiece 33 would be inserted into patient's mouth such that no air can escape through the patient's mouth at functional block 700. The pneumatic abdomen strap 311 would then be wrapped around the patient's abdomen at functional block 710. The second pump 312 then applies pressure or inflates the pneumatic abdomen strap 311 to push up the diaphragm of the patient and prevent it from expanding downwards. In one embodiment, this second pump 312 is integrated into the ventilator or pump 38, which also applies pressure and pumps room air through an air tube to the patient at functional block 720. In addition, the tube contains the bacterial air filter 34 to reduce or prevent any bacteria or particles from entering the patient. The tube also contains the one-way valve 35 so air flows only into but not out of the patient to minimize cross infection. The pressure release valve 37 is also present to prevent over-pressure. The second or external reference pressure sensor 36 within the air tube then measures the pressure in the air tube which is equivalent to the airway pressure of the patient. The computer 39 monitors the airway pressure through a communication link (e.g., a wired communication link) 310*a* connected to the ventilator or pump 38, and the computer 39 monitors the implanted sensor pressure through the wireless link 310*b* to the CRM device 31 at functional block 730. The computer 39 then increases the ventilator or pump pressure periodically while the data from both sensors 32 and 36 are recorded. The ventilator or pump 38 is then deflated to bring down the pressure of the patient's lung at functional block 740. The mouthpiece 33 and the abdomen strap 311 are then removed from the patient at functional block 750. The computer 39 calculates the calibration constants, gain ($\alpha$) and offset ($\beta$) based on $P_{imp}=\alpha P_{ext}+\beta$ through regression analysis or other suitable method at functional block 760. To complete the calibration, the calibration constants are then sent across the wireless link 310*b* to the CRM device 31 to calibrate the sensor 32 at functional block 770.

Figure 8:
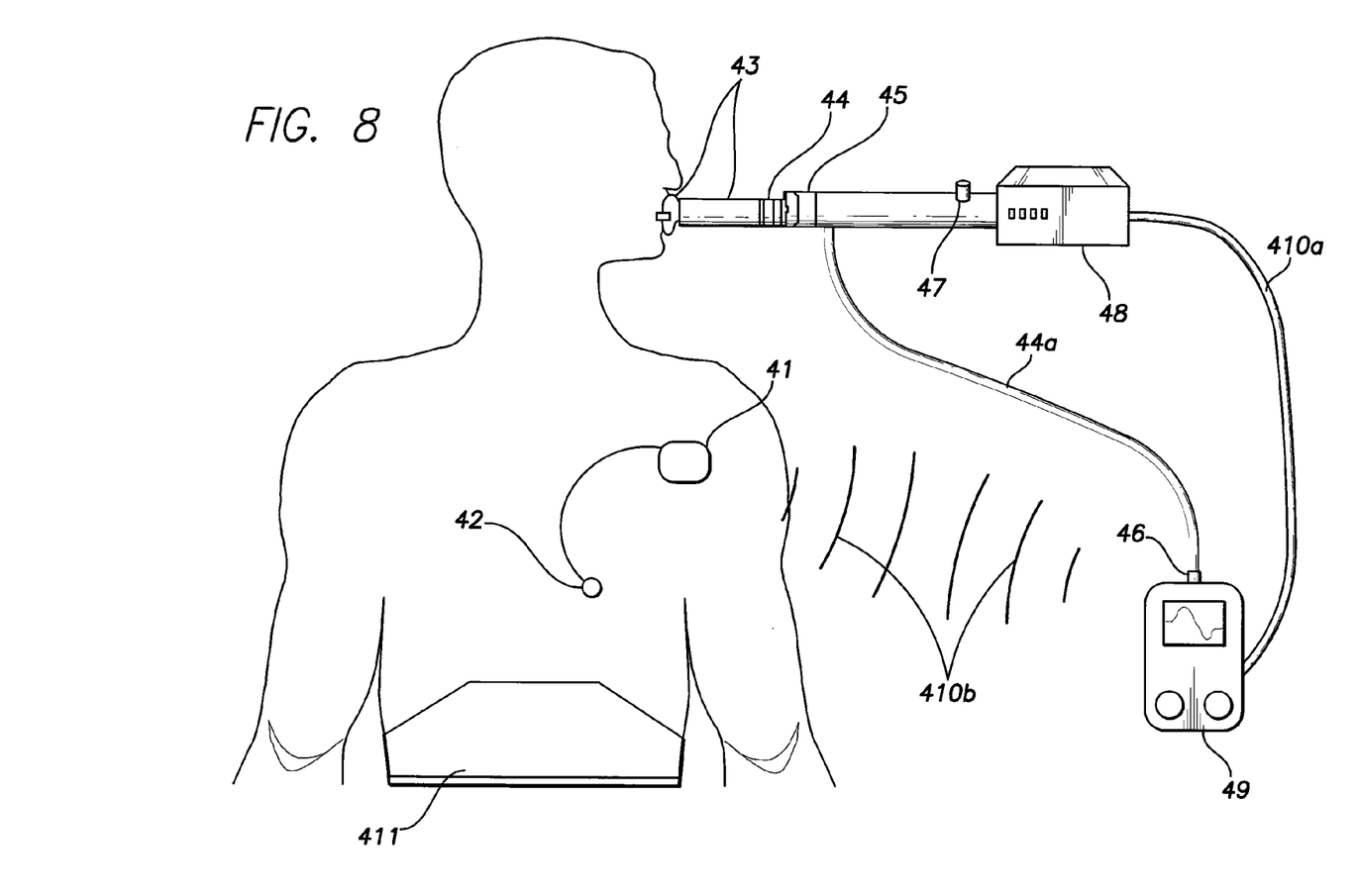
FIG. 8 is a simplified diagram of one embodiment of an implantable sensor calibration system having an adjustable abdomen strap.

Referring to FIG. 8, a calibration system in accordance with another embodiment of the present invention includes a disposable mouthpiece (e.g., a rubber mouthpiece) 43 connected with a ventilator or pump 48 through a bacterial air filter 44 and an optional one-way valve 45. A pressure release valve 47 may also be placed in the system to prevent over-pressure. An adjustable abdomen strap 411 is used to keep the patient's diaphragm from expanding. A second pressure sensor (e.g., an external reference pressure sensor) 46 is connected to a personal digital assistant (PDA) 49 to measure the airway pressure of the patient which will stabilize to be equal to the LAP. Here, the second pressure sensor 46 of the PDA 49 is connected with the ventilator or pump via a link (e.g., an air tube line) 46*a*. The PDA 49 then calculates the calibration constants and transmits the data to a CRM device 41 for controlling or managing a first or implanted pressure sensor 42 via a wireless communication link 410*b* to calibrate the first or implanted pressure sensor 42.

In operation, the patient would be instructed to relax and the disposable mouthpiece 43 would be inserted into patient's mouth such that no air can escape through the patient's mouth. The adjustable strap 411 would then be wrapped tightly around the patient's abdomen to push up the diaphragm of the patient and prevent it from expanding downwards. The ventilator or pump 48 then applies pressure and pumps room air through an air tube to the patient. In addition, the tube contains the bacterial air filter 44 to reduce or prevent any bacteria or particles from entering the patient. The tube also contains the one-way valve 45 so air flows only into but not out of the patient to minimize cross infection. The pressure release valve 47 is also present to prevent over-pressure. The second or external reference pressure sensor (e.g., an accurate external reference pressure sensor) 46 integrated within the PDA 49 then measures the pressure in the air tube via the air line 46 connected to the air tube. The measured pressure is equivalent to the airway pressure of the patient. The PDA 49 monitors the airway pressure to control the ventilator or pump 48 through a communication link (e.g., a wired communication link) 410*a*, and the PDA 49 monitors the implanted sensor pressure through the wireless link 410*b* to the CRM device 41. The PDA 49 then increases the ventilator or pump pressure periodically while the data from both sensors 42 and 46 are recorded. The mouthpiece 43 and the abdomen strap 411 are then removed from the patient. The PDA 49 calculates the calibration constants, gain ($\alpha$) and offset ($\beta$) based on $P_{imp}=\alpha P_{ext}+\beta$ through regression analysis or other suitable method. The calibration constants are then sent across the wireless link 410*b* to the CRM device 41 to calibrate the sensor 42.

Figure 9:
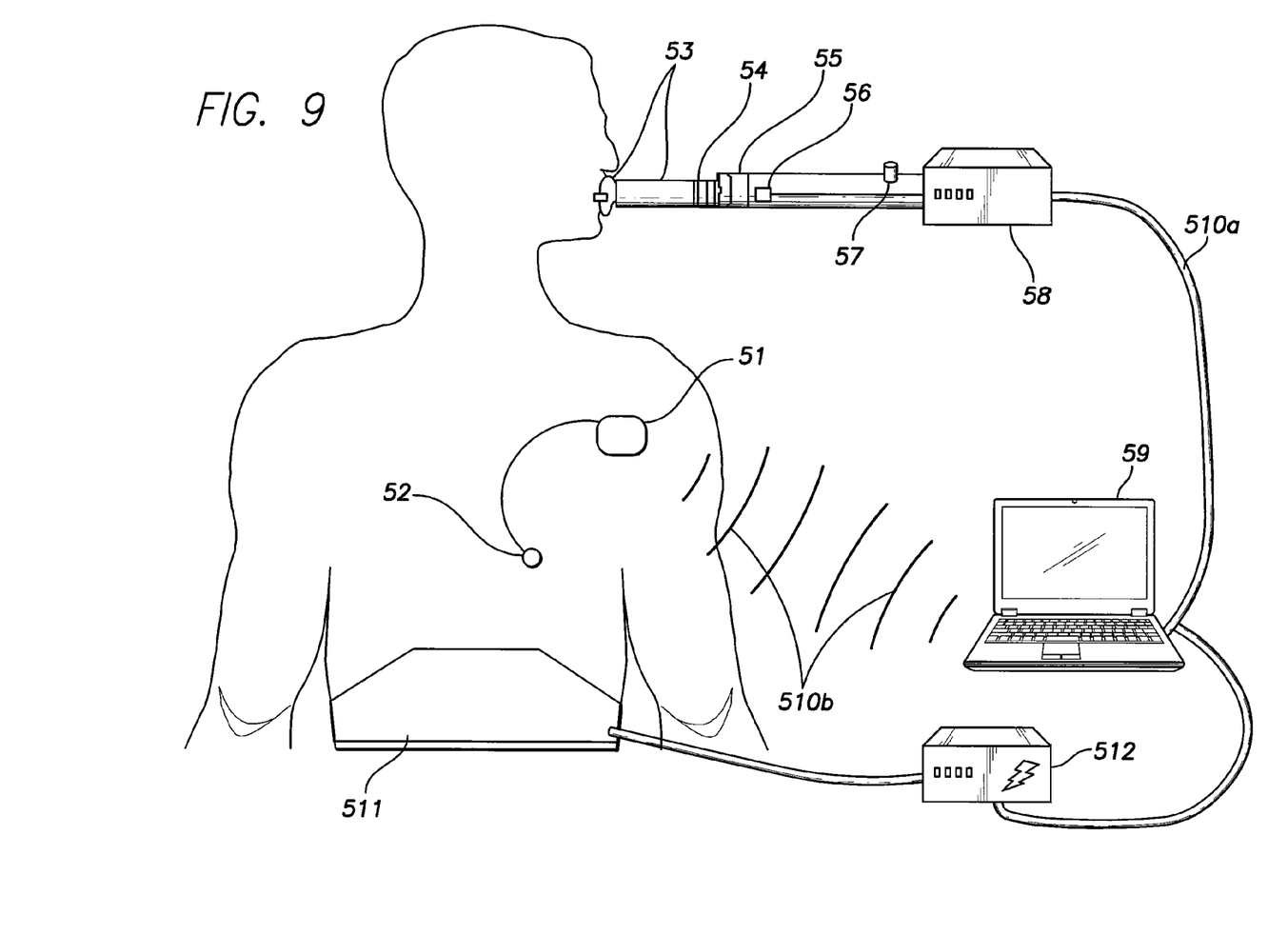
FIG. 9 is a simplified diagram of another embodiment of an implantable sensor calibration system having an abdominal muscle stimulation strap.

Referring to FIG. 9, a calibration system in accordance with another embodiment of the present invention includes a disposable mouthpiece (e.g., a rubber mouthpiece) 53 connected with a ventilator or pump 58 through a bacterial air filter 54 and an optional one-way valve 55. A second pressure sensor (e.g., an external reference pressure sensor) 56 is connected to the ventilator or pump 58 to measure the airway pressure of the patient which will stabilize to be equal to the LAP. A pressure release valve 57 may also be placed in the system to prevent over-pressure. A muscle stimulator 512 controlled by a computer 59 stimulates (e.g., electrically stimulates) the abdominal muscles via an abdominal muscle stimulation strap 511. The computer 59 then calculates the calibration constants and transmits the data to a CRM device 51 for controlling or managing a first or implanted pressure sensor 52 via a wireless communication link 510b to calibrate the first or implanted pressure sensor 52.

In operation, the patient would be instructed to relax and the disposable mouthpiece 53 would be inserted into patient's mouth such that no air can escape through the patient's mouth. The abdominal muscle stimulation strap 511 would then be wrapped around the patient's abdomen. The muscle stimulator 512 then controls the stimulation strap 511 to cause the abdomen to contract and to push up the diaphragm of the patient and prevent it from expanding downwards. The ventilator or pump 58 then applies pressure and pumps room air through an air tube to the patient. In addition, the tube contains the bacterial air filter 54 to reduce or prevent any bacteria or particles from entering the patient. The tube also contains the one-way valve 55 so air flows only into but not out of the patient to minimize cross infection. The pressure release valve 57 is also present to prevent over-pressure. The second or external reference pressure sensor 56 within the air tube then measures the pressure in the air tube which is equivalent to the airway pressure of the patient. The computer 59 monitors the airway pressure through a communication link (e.g., a wired communication link) 510a connected to the ventilator or pump 58, and the computer 59 monitors the implanted sensor pressure through the wireless link 510b to the CRM device 51. The computer 59 then increases the ventilator or pump pressure periodically while the data from both sensors 52 and 56 are recorded. The mouthpiece 53 and the abdomen strap 511 are then removed from the patient. The computer 59 calculates the calibration constants, gain ($\alpha$) and offset ($\beta$) based on $P_{imp}=\alpha P_{ext}+\beta$ through regression analysis or other suitable method. The calibration constants are then sent across the wireless link 510b to the CRM device 51 to calibrate the sensor 52.

In one embodiment, a CRM similar to that shown in FIGS. 2, 5, 6, 8, or 9 is a pacemaker, a defibrillator, a implantable cardioverter defibrillator (ICD), or any other suitable cardiac device(s). It is to be appreciated and understood that other implantable devices, including those that are not necessarily used specifically with the heart, may be used.

According to one embodiment of the present invention, calibration of a first pressure sensor is periodically checked at any suitable time or location, such as during visits to the physician's office, by applying pressure through an air tube to a human patient using a pre-calibrated apparatus containing a second pressure sensor similar to that shown in FIGS. 2, 5, 6, 8, or 9.

The first and second sensor signals are indicative of pressures in first and second locations, respectively. In one embodiment, the first and second sensor signals are used to determine a calibration constant (or constants). In one embodiment, the calibration constant is based upon the difference between the two sensor signals. Alternatively, the calibration constant is based upon any calculable relationship between the pressures at the first and second locations.

In one embodiment, once a calibration constant is determined, the pressure measurement system is calibrated. For example, if the calibration constant indicates an offset value, an offset error, a DC offset, or a gain, the calibration constant is stored in a memory location, and combined by addition (or subtraction, or any other suitable way known to those skilled in the art) to a subsequent pressure measurement taken during clinical diagnosis. In one embodiment, by adding (or subtracting) the calibration constant, calibrated output of the pressure measurement system is achieved. In one embodiment, a calibrator is used to calibrate the pressure measurement system. In one embodiment, as known to those skilled in the art, the calibrator includes the electronics, hardware, software and firmware required to calculate, store, and later apply the parameters and values used to calibrate the pressure measurement system. In one embodiment, the calibrator components include, or implement, various algorithms to calculate, store, and later apply the parameters and values used to calibrate the pressure measurement system. For example, in one embodiment, calibration software implements an algorithm that multiplies a gain factor to a pressure signal received from a pressure measurement system, and then adds an offset value to the product.

In one embodiment, a comparator is used to compare the pressures measured by the pressure measurement system. In one embodiment, the comparator is a computer, a microprocessor, or an electronic circuit. The comparator can also comprise software with appropriate analog to digital circuitry. As is known to those skilled in the art, the output of such comparator may include an electrical signal or an analog or digital value indicative of the differences in measured pressures. In one embodiment, the comparator includes, but is not limited to, the electronics, hardware, software and firmware required to compare such pressure measurements. Such comparators are well known to those skilled in the art.

In one embodiment, once a calibration constant is determined, the calibration constant is compared to a predetermined calibration constant tolerance range. If the calibration constant falls within the tolerance range, the calibration of the system is left unchanged. In one aspect, if the calibration constant falls outside the tolerance range, the pressure measurement system is calibrated as described, for example, above. In one embodiment, the calibration constant tolerance range is at least as wide as the error in determining the calibration constant itself. In a further embodiment, the tolerance range is specified such that changes of the calibration constant within the tolerance range produce pressure measurement changes that are medically insignificant.

One skilled in the art will appreciate that this method of calibration using a transient perturbation of pressure in an adjoining structure is applicable whether sensor(s) are measuring gauge pressure relative to atmospheric, or if they are referenced to some other pressure, or absolute pressure. In one embodiment, the sensors are not calibrated with respect to atmospheric pressure, but are calibrated with respect to each other. For example, in one embodiment, gauge pressure can be derived by measuring the pressure difference between two sensors, each separately calibrated and referenced to absolute pressure.

In one embodiment, the system to be calibrated includes at least one implanted pressure sensor disposed to measure the pressure at one or more locations within the body, and at least one external pressure sensor disposed to measure the atmospheric pressure outside the body. In this embodiment, the quantities of interest are the differences between the pressures at the one or more locations within the body and the atmospheric pressure outside the body. When pressure is expressed as a difference from atmospheric pressure, the pressure is commonly referred to as a "relative pressure" or a "gauge pressure." In one embodiment, both the one or more implanted sensors and the at least one external sensor are calibrated together to calibrate the gauge pressure for drift of both the implantable and external sensors. In this embodiment, neither the implanted sensor nor external sensor need be accurately calibrated on an absolute pressure scale; it is required to calibrate only the difference between the pressure within the body and the exterior atmospheric pressure. This "relative calibration" requires less information than absolute calibration of both the implanted and external pressure sensors.

In one embodiment, two linear pressure sensors, one implanted and one external, each with unknown gain and offset, provide four parameters to be determined during calibration to obtain absolute calibration. However, if relative calibration is sufficient, it will be clear that only three parameters need be determined—the two gain parameters and the difference between the two offset parameters. Because the gauge pressure is calculated by subtracting the measured external pressure from the measured internal pressure, it is not affected by the values of the individual sensor offsets, only by the difference between the offsets.

In one embodiment, an implanted pressure sensor is recalibrated prior to delivering therapy based on pressure measurements whenever the measured ambient pressure or internal physiologic pressure falls outside a previously determined valid range. The therapies include, but are not limited to, automatic drug delivery devices, implanted cardiac devices, such as those discussed above, and oral drug management systems. In this embodiment of the invention, the ambient pressure and mean first location pressure are stored in the device's memory. Each time the device measures pressure, the measured and ambient pressures are, compared against the stored baseline values. If either the ambient or the internal pressure differs by more than a valid calibrated range with respect to its baseline value, the patient is instructed to perform a recalibration or to contact his physician. In another embodiment of the invention, automatic notification is sent to a remote site whenever ambient or internal pressures are outside a valid calibrated range. In a further embodiment of the invention, the system is programmed to suspend any pressure-based changes in therapy whenever the ambient or the internal pressures are outside a valid calibrated range until a recalibration is performed. In another embodiment of the invention, the temperature at the time the external ambient pressure sensor is calibrated will be also stored in memory. If the temperature at the time of a subsequent measurement is outside the range for which the temperature compensation of the external sensor is valid, the patient will be instructed to wait until the temperature comes back into the valid range before making the measurement. In yet another embodiment of the present invention, the date of each or the last recalibration is stored in memory. The patient will be directed to perform a recalibration or contact his physician before the pressure data is used to affect therapy.

It should be appreciated from the above that the various structures and functions described herein may be incorporated into a variety of apparatuses (e.g., a stimulation device, a lead, a monitoring device, etc.) and implemented in a variety of ways. Different embodiments of the implantable device may include a variety of hardware and software processing components. In some embodiments, hardware components such as processors, controllers, state machines and/or logic may be used to implement the described components or circuits. In some embodiments, code such as software or firmware executing on one or more processing devices may be used to implement one or more of the described operations or components.

The components and functions described herein may be connected and/or coupled in many different ways. The manner in which this is done may depend, in part, on whether and how the components are separated from the other components. In some embodiments some of the connections and/or couplings represented by the lead lines in the drawings may be in an integrated circuit, on a circuit board or implemented as discrete wires or in other ways.

In view of the foregoing, an embodiment of the invention described herein generally relates to an economical, repeatable, and non-invasive method and apparatus for the calibration of pressure sensors that can minimize patient discomfort and risk of infection.

While certain exemplary embodiments have been described above in detail and shown in the accompanying drawings, it is to be understood that such embodiments are merely illustrative of and not restrictive of the broad invention. In particular, it should be recognized that the teachings of the invention apply to a wide variety of systems and processes. It will thus be recognized that various modifications may be made to the illustrated and other embodiments of the invention described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A calibration system for calibrating a first pressure sensor configured to output pressure measurements based on at least one calibration constant, the first pressure sensor coupled to a management device implanted into a human patient, the calibration system comprising:

a pump configured to output air through an output port;

a mouthpiece defining a passageway having a distal end configured for coupling with a human mouth and a proximal end configured for coupling with the output port;

a second pressure sensor coupled to the passageway and configured to measure the pressure within the passageway; and a computer coupled to the pump, first pressure sensor and second pressure sensor and configured to cause the pump to output air into the passageway, and monitor pressures measured by the first pressure sensor and the second pressure sensor, wherein the computer is configured to calculate the at least one calibration constant based on the pressures measured by the first pressure sensor and the second pressure sensor and to provide the at least one calibration constant to the management device coupled to the first pressure sensor to calibrate the first pressure sensor.

2. The calibration system of claim 1, further comprising a one-way valve coupled between the pump and the mouthpiece and configured to allow air to flow from the proximal end of the passageway through the distal end of the passageway but not from the distal end of the passageway through the proximal end of the passageway.

3. The calibration system of claim 1, further comprising a pressure release valve coupled between the pump and the mouthpiece to prevent an over-pressure effect.

4. The calibration system of claim 1, wherein the computer sends the at least one calibration constant to the management device through a wireless link to calibrate the first sensor.

5. The calibration system of claim 1, wherein the computer includes a video monitor configured to display the pressures measured by the first pressure sensor and the second pressure sensor.

6. The calibration system of claim 1, wherein the management device is a cardiac management device.

7. The calibration system of claim 1, wherein the second pressure sensor is an external reference pressure sensor.

8. The calibration system of claim 1, wherein the second pressure sensor is integrated within the computer.

9. The calibration system of claim 1, wherein the first pressure sensor is a left atrial pressure sensor.

10. The calibration system of claim 1, further comprising:
 a pneumatic abdomen strap configured to wrap around the abdomen of the patient; and
 a second pump coupled to the pneumatic strap and configured to inflate the pneumatic abdomen strap.

11. The calibration system of claim 10, wherein the computer controls the second pump to inflate the pneumatic abdomen strap to push up the diaphragm of the human patient and prevent the diaphragm from expanding downwards.

12. The calibration system of claim 10, wherein the second pump configured to inflate the pneumatic abdomen strap is integrated into the pump configured to provide the pressure to the mouthpiece.

13. The calibration system of claim 1, further comprising:
 an abdominal muscle stimulation strap configured to wrap around the abdomen of the patient; and
 a muscle stimulator coupled to the abdominal muscle stimulation strap and configured to stimulate the abdominal muscle of the human patient via the abdominal muscle.

14. The calibration system of claim 13, wherein the computer controls the muscle stimulator to contract the abdominal muscle to push up the diaphragm of the human patient and prevent the diaphragm from expanding downwards.

15. The calibration system of claim 1, further comprising:
 an adjustable abdomen strap configured to wrap around the abdomen of the patient and to keep the diaphragm from expanding.

\* \* \* \* \*